United States Patent [19]

Gaetjens

[11] Patent Number: 5,134,071
[45] Date of Patent: Jul. 28, 1992

[54] POLYMERIZATION AND COPOLYMERIZATION OF PROTEINS

[75] Inventor: Eric Gaetjens, Leonia, N.J.

[73] Assignee: State University of New York, Albany, N.Y.

[21] Appl. No.: 307,065

[22] Filed: Feb. 6, 1989

[51] Int. Cl.$^5$ .................. C12N 9/96; C07K 17/02
[52] U.S. Cl. .................. 435/188; 435/189; 435/190; 435/192; 435/194; 435/207; 435/964; 530/345; 530/362; 530/363; 530/367; 530/391.9; 530/404; 530/405; 530/408; 530/409; 530/807; 530/812
[58] Field of Search .......... 530/362, 363, 404, 390, 530/408, 345, 367, 391, 399, 405, 409, 807, 812; 435/188, 189, 190, 192, 194, 207, 964

[56] References Cited

U.S. PATENT DOCUMENTS

| | | | |
|---|---|---|---|
| 4,004,979 | 1/1977 | Avrameas et al. | 435/176 |
| 4,220,565 | 9/1980 | Katz | 525/54.1 |
| 4,515,920 | 5/1985 | Erickson | 525/54.11 |
| 4,671,958 | 6/1987 | Rodwell et al. | 424/85.91 |
| 4,687,732 | 8/1987 | Ward et al. | 435/6 |
| 4,711,951 | 12/1987 | Axen et al. | 530/323 |

OTHER PUBLICATIONS

Blair et al (1983) J. Immunol. Methods 59:129–143.
Kennedy et al (1976) Clin. Chim. Acta 70:1–36.
Carlsson et al., Biochem. J., 173, 723–737 (1978).
Yoshitake et al., Eur. J. Biochem., 101, 395–399 (1979).
Poznansky et al., Cancer Research, 42, 1020–1025 (1982).
Poznansky et al., Science, 223, 1304–1306 (1984).
Ahmed et al., Trends in Biotechnology, 6, 246–251 (1988).
Leary et al., Proc. Natl. Acad. Sci. USA, 80, 4045–4049 (1983).

*Primary Examiner*—Christine Nucker
*Assistant Examiner*—Kay K. Kim
*Attorney, Agent, or Firm*—Hoffmann & Baron

[57] ABSTRACT

A method for producing a polyprotein having at least 10 units, and often as many as 50 to 100 and more units held together by sulfur to sulfur or sulfur to carbon bonds is disclosed. Each unit comprises a protein and one or more heterobifunctional reagents. One functional group of the reagent is capable of forming a covalent bond with an amino group, permitting the reagent to bind to a protein. The other functional group of the reagent is capable of forming a covalent bond with a thiol group so as to form the covalent sulfur-carbon or sulfur-sulfur bond with another heterobifunctional reagent bonded to another protein.

48 Claims, No Drawings

POLYMERIZATION AND COPOLYMERIZATION OF PROTEINS

The present invention is directed to a method for conjugating proteins so as to form polyproteins and copolyproteins as well as the polyproteins and copolyproteins formed by such methods.

BACKGROUND OF THE INVENTION

Interest has been growing in protein conjugates formed by chemically linking two or more proteins. For example, cytotoxins may be linked to a monoclonal antibody specific for cells of diseased tissue or tumors. The monoclonal antibody seeks out the undesired cell and the cytotoxin destroys it without affecting normal and healthy cells. The commercial value of such conjugates was discussed in an article on page D6 of the *New York Times* of Jul. 1, 1987 in an article entitled "Aiming 'Bullets' At Disease".

A conjugate can include two proteins, or more than two proteins. An example of a conjugate having many protein units was reported by Poznansky et al. in *Science*, 223, 1304–1306 (1984). The conjugate described by Poznansky, et al. contained the enzyme 1,4-glucosidase, albumin and insulin in a ratio of 1:10:60, and reportedly had an average molecular weight of $1.1 \times 10^6$. The purpose of the conjugate was an improved treatment of patients suffering from low glycogen levels in muscle cells of cardiac and respiratory tissue due to type 2 glycogenesis. Conjugating the enzyme to albumin was reported to have rendered the enzyme both non-antigenic and non-immunogenic.

Polyproteins having a different purpose were disclosed by Ward, et al., U.S. Pat. No. 4,687,732. The Ward, et al. patent discloses visualization polymers linked to detecting agents. The visualization polymers contain proteins capable of being visualized when bound with a substrate. The detecting agent is specific for a target molecule that is the subject of an assay. For example, if the molecule being assayed is an antigen, the detecting agent may be an antibody. The multiple units of the visualization polymer amplify the signal that would be expected from binding the detecting agent to the target molecule.

Protein conjugates are prepared by linking proteins together using bifunctional reagents. The bifunctional reagents can be homobifunctional or heterobifunctional.

Homobifunctional reagents are molecules with at least two identical functional groups. The functional groups of the reagent generally react with one of the functional groups on a protein, typically an amino group.

Examples of homobifunctional reagents include glutaraldehyde and diimidates. An example of the use of glutaraldehyde as a cross-linking agent was the preparation of the enzyme-albumin-insulin polymer by Poznansky as described above. (See also Poznansky et al, *Science*, 223, 1304–1306 (1984)). The use of diimidates as a cross linking agent was described by Wang, et al. in *Biochemistry*, 16, 2937–2941 (1977).

Heterobifunctional regents have at least two different functional groups, each of which is capable of reacting with a different functional group of a protein. The different functional groups of a protein are typically an amino group and a thiol group.

The heterobifunctional reagents provide a more sophisticated method for linking two proteins. An example of a heterobifunctional reagent is N-succinimidyl 3-(2-pyridyldithio)propionate (SPDP). SPDP was described by Carlsson et al. in *Biochem. J.*, 173, 723–737 (1978). The linking of two proteins, arbitrarily referred to as protein-1 and protein-2, is provided in scheme 1.

Another heterobifunctional reagent for linking proteins is succinimidyl 4-(N-maleimidomethyl)cyclohexane-1-carboxylate (SMCC), which is described by Yoshitake et al., *Eur. J. Biochem*, 101, 395–399 (1979). The use of SMCC to form a conjugate of two proteins may be described as shown in Scheme 2.

A number of additional heterobifunctional reagents for forming conjugates of two proteins is described by Rodwell et al., U.S. Pat. No. 4,671,958. Strategies for designing antibody-conjugates are reviewed by Ahmad et al., *Trends in Biotechnology*, 6, 246–251 (1988).

The disadvantage of the homobifunctional reagents is the random attachment of different proteins. In attempting to link a first protein with a second protein by means of a homobifunctional reagent, one cannot prevent the linking of the first protein to each other and of the second to each other.

The disadvantage of homobifunctional reagents is overcome by means of the heterobifunctional reagents. With the heterobifunctional reagents, one can control the sequence of reactions, and combine proteins at will.

Suggestions have been made to extend the use of heterobifunctional reagents beyond the preparation of protein conjugates containing two proteins. Thus, Carlsson et al., who disclose the use of SPDP to link proteins (see above) suggest at pages 733 and 734 of their article the possibility of producing tri- and tetra-protein conjugates by increasing the number of heterobifunctional reagents in the proteins. No experimental details of how to do so, however, are provided.

Similarly, Ward et al., U.S. Pat. No. 4,687,732, which discloses polyproteins for visualizing target molecules (see above), suggests the possibility of using heterobifunctional reagents for preparing the polymers. No experimental details are given, however. Only the homobifunctional reagent disuccinimidyl suberate is exemplified for linking proteins into the visualization polymer. See column 23, line 67 et sec. of U.S. Pat. No. 4,687,732 and Leary, et al., *Proc. Natl. Acad. Sci. USA*, 80. 4045–4049 (1983).

The ability to carry out rational schemes for producing polymers wherein the monomer units are proteins is desirable. It is not enough, however, merely to state that heterobifunctional reagents can be used to prepare polymers of proteins in the same way they are used to prepare dimers. There is a need, therefore, for a method of producing conjugates comprising polymers of proteins using heterobifunctional reagents to link the proteins together. It is an object of the present invention to provide such a method. It is a further object of the invention to prepare such polyproteins.

SUMMARY OF THE INVENTION

These and other objectives as will be apparent to those of ordinary skill in the art have been met by providing a method for producing a polyprotein having at least 10 units, and often as many as 50 to 100 and more units, held together by covalent bonds, such as sulfur to sulfur or sulfur to carbon bonds. Each unit comprises a protein and one or more heterobifunctional reagents. One functional group of the heterobifunctional reagent is capable of forming a covalent bond with an amino group, permitting the reagent to bind to a protein. The other functional group of the reagent is either a thiol group, a group capable of being converted into a thiol group or a group capable of forming a covalent bond with a thiol group. The combination of the thiol group and the group capable of forming a covalent bond with a thiol group leads to the covalent bond between the two protein units in the polyprotein. The covalent bond is usually a sulfur-carbon or sulfur-sulfur bond.

The first step of the method comprises forming a first protein-heterobifunctional reagent complex by treating a first protein with a sufficient amount of a heterobifunctional reagent so as to form a covalent bond between amino groups of the first protein and 3 to 5 molecules of the reagent per protein molecule. Similarly, a second protein-heterobifunctional reagent complex is formed by treating a second protein with a sufficient amount of a heterobifunctional reagent so as to form a covalent bond between amino groups of the second protein and at least 5 molecules of the reagent per protein unit. In the final step, the first protein-reagent complex and the second protein-reagent complex are joined by forming covalent bonds into a polyprotein having at least 10 units, and often as many as 50 to 100 or more units.

ABBREVIATIONS

In order to assist in reading this specification, the following list of abbreviations is provided:

Av, egg white avidin;
DTNB, 5,5'-dithio-bis-(2-nitrobenzoic acid);
DTT, dithiothreitol;
FITC, fluorescein isothiocyanate;
HSA, human serum albumin;
HSA-FL, fluorescein labeled HSA;
HRP, horseradish peroxidase;
IgG, immunoglobin G;
MCC, 4(N-maleimidomethyl)cyclohexane-1-carboxyl-;
2-ME, 2-mercaptoethanol;
merthiolate, ethyl (2-mercaptobenzoate-S) mercury sodium salt;
NEM, N-ethylmaleimide;
PBS, phosphate buffer solution containing dilute salt;
PDP, 3-(2-pyridyldithio)propionyl-;
SDS, sodium dodecylsulfate;
SMCC, succinimidyl 4-(N-maleimidomethyl)cyclohexane-1-carboxylate;
SPDP, N-succinimidyl 3-(2-pyridyldithio)propionate;
TP, 3-thiopropionyl.

DETAILED DESCRIPTION OF THE INVENTION

The present invention is directed toward a method for linking at least 10 protein units, and often as many as 50 to 100 and more units, into a polyprotein by means of a heterobifunctional reagent. The heterobifunctional reagent has at least two different functional groups. One of the functional groups forms a covalent bond with amino groups on proteins. The covalent bond will usually be an amido or imido bond. The functional group that forms a covalent bond with amino groups may, for example, be an activated carboxylate group, a halocarbonyl group, or an ester group. The preferred halocarbonyl group is a chlorocarbonyl group. The ester groups are preferably reactive ester groups such as, for example, an N-hydroxysuccinimide ester group.

The other functional group is the reactive group, which is either a thiol group, a group capable of being converted into a thiol group, or a group that forms a covalent bond with a thiol group. The covalent bond will usually be a thioether bond or a disulfide. The reactive group that forms a covalent bond with a thiol group may, for example, be a double bond that reacts with thiol groups or an activated disulfide. The most common reactive group containing a double bond capable of reacting with a thiol group is the maleimido group, although others, such as acrylonitrile, are also possible. A reactive disulfide group may, for example, be a 2-pyridyldithio group or a 5,5'-dithio-bis-(2-nitrobenzoic acid) group.

Some examples of heterobifunctional reagents containing reactive disulfide bonds include N-succinimidyl 3-(2-pyridyldithio)propionate, 2-iminothiolane, sodium S-4-succinimidyloxycarbonyl-α-methylbenzylthiosulfate, 4-succinimidyloxycarbony-α-methyl-(2-pyridyldithio)toluene. N-succinimidyl 3-(2-pyridyldithio)propionate is preferred.

Some examples of heterobifunctional reagents comprising reactive groups having a double bond that reacts with a thiol group include SMCC, succinimidyl m-maleimidobenzoate, succinimidyl 3-(maleimido)propionate, sulfosuccinimidyl 4-(p-maleimidophenyl)butyrate, sulfosuccinimidyl 4-(N-maleimidomethylcyclohexane-1-carboxylate, maleimidobenzoyl-N-hydroxysuccinimide ester.

Any oligopeptide, polypeptide, or protein may be used in the method of the present invention. Unless otherwise specified, the term protein will be understood in the present specification and claims to encompass oligopeptides and polypeptides.

The polyproteins formed by the method of the invention have at lest 10 units, and often as many as 50 to 100 and more units. There is no necessary upper limit to the number of units the polyprotein may have. The molecular weight of the polyproteins of the present invention is typically at least $2 \times 10^6$ and may be at least $10 \times 10^6$ and even sometimes at least $20 \times 10^6$ The maximum molecular weight is the molecular weight at which the polyprotein begins to sediment as a gel. This molecular weight may be about $50 \times 10^6$ or $100 \times 10^6$ or even higher.

The useful ratio of units of the first protein to the second protein in the polyproteins is generally between 1:0.25–1:10. More preferably, the ratio of 1:1–1:4.

The utility of polyproteins of the present invention is increased if the polyproteins are soluble in water. The polyproteins of the present invention usually retain substantially the same solubility properties as the protein units that make up the polyprotein. The protein units of the polyprotein and, therefore, the polyprotein itself are generally soluble in water until the point that the solution begins to thicken to a gel. Typically, the solubility of the protein units and of the polyprotein in water is 50 mg/ml, sometimes as high as 100 mg/ml and even higher.

In addition, it is a general, often critical, feature of the present invention that the protein units substantially retain their chemical properties and biological activities in the polyprotein.

Polyproteins that comprise more than one type of protein unit are referred to as copolyproteins. For example, a polyprotein comprising horseradish peroxidase and avidin units is a copolyprotein in accordance with the terminology used in the present specification.

There are various reasons for combining different proteins into a copolyprotein. For example, one of the proteins may be present for the purpose of binding to a target molecule. The target molecule may be attached to a cell, and the binding may occur in vitro or in vivo. Selection of a protein to bind to the target molecule depends on the nature of the target molecule. For example, if the target molecule is antigenic, the binding protein may be the corresponding antibody. The antibody is preferably monoclonal. More preferably, several monoclonal antibodies specific for different epitopes of the antigen are combined in the same polyprotein. Similarly, if the target molecule is a specific sugar, biotin, iminobiotin, specific enzyme substrate, hormone receptor, or polynucleotide, the binding protein may be lectin, avidin, streptavidin, the enzyme, the hormone, or a sequence specific polynucleotide binding protein, respectively. An example of a hormone capable of binding to a specific receptor is insulin. A particularly useful binding protein is avidin, since avidin binds unusually strongly with biotin and may be used in the detection of biotinylated proteins.

After the binding protein binds to the target molecule, the protein (or proteins) linked to the binding protein in the polyprotein acts upon the target molecule or on cells in the vicinity of the target molecule. For example, the protein linked to the binding protein may be a cytotoxin, detection protein or hormone.

Binding protein-cytotoxin conjugates are known as immunotoxins, and may be used to destroy undesirable cells, for example, cells of diseased tissue and tumors. Some examples of cytotoxins useful in the polyproteins of the present invention include, for example, gelonin, pokeweed antiviral protein, ricin, abrin, modeccin, diptheria toxin, and pseudomonas toxin.

Some toxins have two chains, one that is toxic and one that is not toxic. In such cases, the non-toxic chain may be removed, and only the toxic chain linked to the binding protein.

The protein linked to the binding protein in the polyproteins of the invention may also be used to detect and to assay the target molecules, i.e. a detector protein. Detection may be for the purpose of quantifying the target molecule, such as in radioimmunoassay and ELISA techniques. If the target molecules are attached to diseased cells or tissue, the disease may be diagnosed in a patient. The target molecule may be part of the diseased cell, or may be an antibody produced by the patient against an antigen on the diseased cell. Diseases such as AIDS and cancer may be detected in this way.

The detection protein should permit qualitative and quantitative analysis of the target molecule. Usually, the basis for the assay will be spectroscopy, fluorescence, radioactivity or electron density. For example, the protein may contain a tag that produces a measurable signal, such as radioactive iodine, or it may be an enzyme that reacts with a substrate so as to produce a measurable signal. Some examples of such enzymes include alkaline phosphatase, acid phosphatase, peroxidase, galactosidase, glucose oxidase and luciferase.

In order to increase sensitivity, the ratio of the cytotoxin or detection protein linked to the binding protein should be as large as possible. The ratios of different proteins conjugated together in accordance with the present invention are discussed above.

In another embodiment of the invention, a polyprotein backbone consisting essentially of a single protein unit may be prepared. The protein units in the polyprotein backbone contain reactive groups from excess bifunctional reagent still bound to amino groups. These excess reactive groups are chemically unaffected when the polyprotein is formed.

The reactive groups on the polymer backbone may be treated with molecules containing, or modified to contain, thiol groups. Alternatively, reactive groups on the backbone, such as disulfide-containing reactive groups, may be converted to thiol groups and bound to other molecules containing, or modified to contain maleimido or other reactive groups. The molecules that contain or are modified to contain maleimido or other reactive groups are preferable oligopeptides, polypeptides or proteins bound to heterobifunctional reagents.

Accordingly, any proteins, such as those described above, may be added to the polyprotein backbone. This method is more convenient than producing copolyproteins, since stock quantities of the polyprotein backbone containing reactive groups may be prepared. In addition, there is greater flexibility in designing a polyprotein having a single type of protein or various ratios of two or more proteins attached to the polyprotein backbone. Thus, two proteins may be added to the polyprotein backbone by the method described above in ratios of 1:100, 1:10, or 1:1. For example, an immunotoxin should have a large ratio of toxin to binding protein for increased sensitivity.

There should be as many reactive groups as possible on the backbone protein, although not all reactive groups will necessary be available for binding other protein units. If it is desired to reduce the number of reactive groups, they can be treated with non-protein thiol compounds, such as 2-ME. There should, in general, be an average of at least one available reactive group per protein unit in the polyprotein backbone.

Any protein may form the backbone of the polyprotein. This protein will ordinarily serve as a carrier for the proteins attached to the reactive groups. In such cases, the protein units are selected on the basis of convenience. Albumin is a particularly convenient example. The proteins attached to the reactive groups on the polyprotein backbone may be any of the proteins that may comprise the units of the copolyproteins discussed above.

In order to prepare polyproteins by the method of the invention, a first protein-heterobifunctional reagent complex is prepared by treating a first protein with a sufficient amount of a heterobifunctional reagent so as to form covalent bonds between the amino groups of the first protein and 3-5 molecules of the reagent per protein molecule. Since the reaction between the heterobifunctional reagent and the protein is normally incomplete, an excess of the reagent is usually preferable.

In order to achieve the critical 3-5 molecules of reagent per protein molecule, a molar excess of bifunctional reagent over protein of, for example, at least two should be used. Thus, if three molecules of reagent per protein molecule is desired, a molar excess of bifunctional reagent over protein of at least six would be used. There is no upper limit, although a molar excess of more than about ten leads to wastefully large amounts of unreacted heterobifunctional reagent.

For example, when horseradish peroxidase was treated with a ten molar excess of SPDP, a complex comprising 4.2 moles of PDP per mole of HRP was obtained. Similarly, when bovine immunoglobulin G(IgG) was treated with a 5 molar excess of SMCC, a complex comprising 3.2 MCC groups per IgG molecule was obtained. The activity of the HRP was not significantly affected by the addition of the PDP groups. The reaction may conveniently be conducted by adding the bifunctional reagent in a water soluble organic solvent such as ethanol. The reaction temperature is not critical, and may conveniently vary between zero degrees centigrade and room temperature. The pH of the aqueous protein solution should be high enough to prevent protonation of amino groups, but is otherwise not critical, and may vary, for example, between 8 and 9.5.

The heterobifunctional reagent is joined to the protein by means of a covalent bond between free amino groups of the protein and the group on the reagent that reacts with amino groups. Sources of amino groups on the protein include the N-terminal amino acid and internal amino acid residues containing amino groups other than the α-amino group, such as arginine, hydroxylysine, and lysine residues.

A second protein-heterobifunctional reagent complex is formed under essentially the same reaction conditions as those for forming the first complex. In the second complex, however, the ratio of reactive groups per protein unit is at least about 5, preferably at least about 20, and more preferably at least about 30. The upper limit is not critical, and is limited only by the number of amino groups that are available in the protein for bonding with the heterobifunctional reagent. Typically, the number of heterobifunctional groups in the second protein-heterobifunctional reagent is 20-35, and usually not more than 50.

At least one of the reactive groups of the first or second protein-heterobifunctional reagent is capable of forming a covalent bond with a thiol group. The other reactive group is a thiol group. The thiol group is preferably derived from a reactive group that can be directly converted into a thiol group. A group may be directly converted into a thiol group if the conversion is a simple, usually one step, or at least one pot, reaction. Although some of the thiol groups that bind to the reactive groups may be derived from naturally occurring cysteine residues in the protein, most, if not all, of the thiol groups are derived from one of the heterobifunctional reagents. It is this requirement for external thiol groups that permits control over the reaction, distinguishing the method from those using homobifunctional reagents, where the cross-linking of proteins is random.

When one of the reactive groups, for example, is a disulfide group, the thiol groups may be formed by reducing the disulfide group with dithiothreitol. The resulting free thiol groups react with reactive groups capable of forming covalent bonds with a thiol group, such as PDP or MCC, linking the protein units.

The thiol groups may be from the first protein-heterobifunctional reagent complex or from the second protein-heterobifunctional reagent complex as described above. It is preferable for the thiol groups, which tend slowly to oxidize, to be derived from the second complex. This is because the second complex contains a larger number of bound heterobifunctional reagents than the first complex. Therefore, the second complex is better able to tolerate the loss of a few thiol groups.

The copolymerization reaction between the protein-heterobifunctional reagent complex containing a reactive group and the protein-heterobifunctional reagent complex containing or modified to contain a thiol group is carried out by mixing the proteins in a molar ratio of, for example, about 1:1 to 1:10, preferably about 1:1 to 1:4, and most preferably about 1:2 irrespective of which complex is in excess. Thus, as shown in Example 1, the copolymerization of PDP-HRP with an average of 4.2 PDP groups per molecule of HRP and TP-Av with an average of 32 TP groups per molecule of Av at 0° C. and a pH of 7.3 wherein the PDP-HRP and TP-Av was equimolar resulted in a copolyprotein containing 1.8 units of Av per unit of HRP. Similarly, as shown in Example 2, the copolymerization of MCC-IgG with an average of 3.2 moles of MCC/mole of IgG and TP-HSA-FL with an average of 37 moles of TP/mole of HSA-FL wherein the molar ratio of MCC-IgG and TP-HSA-FL was about 1:2 at 0.C and a pH of 7.3 resulted in a copolyprotein containing approximately equal amounts of the two protein units.

The copolymerization reaction may be quenched by adding molecules that block the thiol groups, such as N-ethylmaleimide (NEM). Progress of the reaction may be followed by, for example, spectroscopy or high performance liquid chromatography.

The pH of the copolymerization reaction is not critical and may vary, for example, between 6 and 9. The temperature of the reaction is also not critical and conveniently varies between zero degrees centigrade and room temperature.

As is apparent, the advantage of the presently described method for linking proteins is that each protein molecule may be pre-conjugated and purified to contain a defined number of heterobifunctional reagents, thereby allowing control of the outcome of the polymerization reaction and the preparation of tailor-made polyproteins. The small number of heterobifunctional reagents in the first protein-heterobifunctional reagent complex preserves the biological activity of the first protein and, at the same time, limits the number of intermolecule linkages (a key in preventing formation of highly cross-linked, insoluble products). The large number of heterobifunctional reagents in the second protein-heterobifunctional reagent complex provides the driving force for the polymerization process to yield products of high molecular weights, while the excess unreacted groups can be utilized for further chemical modification. Polyproteins in accordance with the present invention typically elute from a Sepharos-4B chromatographic column at the "exclusion volume", corresponding to molecular weights around $10 \times 10^6$ to $20 \times 10^6$.

EXAMPLES

Materials and Methods

Materials. In the examples below, N-ethylmaleimide (NEM) and 5,5'-dithio-bis-(2-nitrobenzoic acid) (DTNB) were from Calbiochem. Dithiothreitol (DTT) was from Sigma. Fluorescein isothiocyanate (FITC) was from Research Organics. N-succinimidyl 3-(2-pyridyldithio)propionate (SPDP) and succinimidyl 4-(N-maleimidomethyl)cyclohexane-1-carboxylate (SMCC) were from Pierce. Sephadex G-25 and Sepharose-4B and -6B were from Pharmacia. Crystalline human serum albumin (HSA) from Sigma was dialyzed and lyophilized. Horseradish peroxidase (HRP) was from Sigma (type VI, cat. no. P-8375) and had an absorbance ratio $A_{403}/A_{280}$ of 3.0. Affinity purified Avidin (Av) was from Sigma (cat. no. A-9275). Immunoglobulin G (IgG) was prepared from normal bovine serum (Gibco) by ammonium sulfate precipitation followed by chromatography on DEAE-Sephacel (Pharmacia) with 0.0175 M $NaH_2PO_4$ at pH 6.3, and lyophilized.

High-Performance Liquid Chromatography (HPLC). All runs were performed using a TSK-G3000 SW gel permeation column of 26 ml bed volume (Beckman) eluted with 0.1 M $NaH_2PO_4$ at pH 7.3 (with 0.1%(w/v) SDS sometimes added) at a flow rate of 1 ml/min. The effluent was monitored at 206 nm using a Waters Model 450 variable wavelength detector. Samples were centrifuged at 2,000 g for 1 min before injection and chromatographed in duplicate. Buffers were degassed daily under reduced pressure.

Sephadex and Sepharose Chromatography. Columns varying from 40-125 ml in bed volume were eluted at room temperature with 0.15 M NaCl containing 25 mM $NaH_2PO_4$ at pH 7.3 (PBS) (with 0.1%(w/v) SDS sometimes added), at a flow rate of 0.5 ml/min. Fractions of 0.5-1.0 ml were collected and the effluent was monitored at 206 nm using an LKB uvicord S. Buffers were degassed under reduced pressure.

Thiol Determination. Assays were performed in duplicate by reacting thiols with 1 mM DTNB at pH 8.2 for 10 min. The thiol content was calculated from absorbance measurements at 412 nm ($A_{412}$) using an extinction coefficient of $13.6 \times 10^3$ $M^{-1}$ $cm^{-1}$ ($E^M_{412}$) (Ellman, Arch. Biochem. Biophys. 82, 70-77 1959)).

Labeling of Human Serum Albumin with FITC (HSA-FL). The procedure is similar to that described by Gaetjens & Pertschuk, J. Steroid Biochem. 13, 1001-1003 (1980). 200 mg of HSA and 20 mg of FITC were reacted in 10 ml of 0.2 M $Na_2CO_3$ at pH 9.5 and 0°, for 8 h. Following dialysis for 24 h against cold water, the preparation was chromatographed on a column of Sephadex G-25 (190 ml bed volume) in water, and the protein was collected in 60-85 ml of effluent and lyophilized. For characterization, a 0.1 mg/ml solution in PBS was prepared from a weighed sample. It showed maximum absorbance at 495 nm and a ratio of $A_{495}/A_{280}$ of 1.6. An extinction coefficient of 5.3 ml $mg^{-1}$ $cm^{-1}$ at 495 nm ($E_{495}^{1\%} = 53$) was calculated. A stoichiometry of 5 moles of FITC bound/mole of HSA was calculated using an $E_{495}^M$ of $78 \times 10^3$ for FITC covalently bound to protein (Holborow & Johnson, Handbook of Experimental Immunology (Weir, D. M., Ed.) pp 571-596, Blackwell Scientific Publications Ltd., Oxford, 1967)).

Fluorescence Measurements. Relative fluorescence emission of protein bound FITC was measured with Gilson Spectra/Glo Filter Fluorometer fitted with filters having excitation and emission maxima at 485 nm and 520 nm, respectively. For measurements, solutions were normalized to an $A_{495}$ of 0.005.

EXAMPLE 1

Copolyprotein of Horseradish Peroxidase and Avidin

A. Conjugation of HRP with SPDP (PDP-HRP). SPDP (450 μl, 18 μmoles) in anhydrous ethanol at room temperature (requires brief warming to dissolve) was added in 4 increments during 4 min and with rapid stirring to 10 mg of HRP in 2.5 ml of 50 mM $NaHCO_3$ at pH 9.0 and 0° C. (solution turns cloudy). Stirring was continued for 30 min at 0° C. The reaction mixture was neutralized with 250 μl of 1 M $NaH_2PO_4$ at pH 7.3, warmed to room temperature, clarified by centrifugation at 12,000 g for 1 min, and chromatographed on a G-25 column (40 ml bed volume). The protein was collected in 17-21 ml of effluent, and the pooled fractions concentrated to a volume of 570 μl by ultrafiltration at 15 0° C. in a Centricon-30 Microconcentrator (Amicon). The concentrate was set aside on ice for characterization and utilized within 2 h of preparation. A protein concentration of 12.6 mg/ml was obtained based upon $A_{403}$ measurements and an $E_{403}^{1\%}$ of 25.5 (Schonbaum and Lo, J. Biol. Chem. 247, 3353-3336 1972)). The number of 3-(2-pyridyldithio)propionyl (PDP) groups conjugated was determined by measuring the increase in $A_{343}$ that occurs when 2-thiopyridone is released from its disulfide linkage by DTT. In a typical assay, a test solution containing 0.54 mg. of PDP-HRP in 1 ml of PBS and having an $A_{343}$ of 0.36 was treated with 0.55 mole of DTT in 1 μl of $H_2O$ (40 fold molar excess over HRP) for 15 min, and yielded an $A_{343}$ of 0.81. The number of PDP groups conjugated/molecule of HRP, which was calculated using an $E_{343}^M$ of $8.08 \times 10^3$ for 2-thiopyridone (Stuchbury et al., Biochem J., 151 417-432 (1975)) was 4.2. Assays were performed in duplicate and agreed within 5%.

B. Thiolation of Av with SPDP (TP-Av). SPDP (215 μl, 8.6 μmoles) in anhydrous ethanol was added during 1 min with rapid stirring to Av (8 mg, 0.12 μmole) in 2 ml of 50 mM $NaHCO_3$ at pH 9.0 and 0° C. (precipitate forms). Stirring was continued for 15 min at 0° C., followed by neutralization with 200 μl of 1 M $NaH_2PO_4$ at pH 7.3. DTT (172 μl, 86 μmoles) at pH 7.3 was next added to reduce PDP-derived disulfide bonds, and stirring was continued at room temperature for 30 min (the precipitate clears in about 15 min). Following centrifugation at 12,000 g for 1 min, the solution was chromatographed on G-25 (40 ml bed volume). Protein was collected in 19-24 ml of effluent, the pooled fractions concentrated to 500 μl by ultrafiltration, and the concentrate set aside on ice in a capped vial for characterization, and utilized within 2 h. A protein concentration of 14.0 mg/ml was determined from $A_{280}$ measurements and an $E_{280}^{1\%}$ of 15.4 (Green and Toms, Biochem. J. 118, 67-70 (1970)). The number of protein bound 3-mercaptopropionyl groups, which was determined by reacting 10 μl (0.14 mg) aliquots with DTNB, was 32 TP groups per molecule of Av.

C. Copolymerization of PDP-HRP and TP-Av. Copolymerization was performed by stirring 263 μl (3.3 mg, 81 nmoles) of PDP-HRP, 400 μl (5.8 mg, 83 nmoles) of TP-Av, and 66 μl of 1 M $NaH_2PO_4$ at pH 7.3 and 0°-4° C. for 65 h in a capped vial. For control, some unreacted PDP-HRP and TP-Av were set aside for the duration of the experiment and examined for the presence of polymer. The progress of the reaction was monitored by diluting 33 μl aliquots at various time intervals in 400 μl of PBS containing 1.3 μmoles of NEM (10 fold molar excess over original TP content of Av), and reacting for 15 min. Following centrifugation, 15 μl aliquots (5 μg HRP and 9 μg Av) of supernatant were subjected to HPLC while the remaining solution (143 μg HRP and 248 μg Av) was chromatographed on Sepharose-4B (40 ml bed volume). After 65 h 520 μl of the reaction mixture was centrifuged at 12,000 g for 1 min to remove insoluble material, diluted with 300 μl of 0.1 M $NaH_2PO_4$ at pH 7.3 containing 20 μmoles of NEM (10 fold molar excess over TP), reacted for 30 min at 0° C., and chromatographed on Sepharose-4B (125 ml bed volume) A polymeric peak was collected in 42-47 ml of effluent and was set aside on ice for characterization. Protein recovery and composition was calculated by $A_{403}$ and $A_{280}$ measurements. There were approximately equal numbers of units of PDP-HRP and TP-Av in the polyprotein.

A portion of the solution with 0.01%(w/v) merthiolate added was kept for 37 days at 0°–4° C., and monitored for peroxidase activity. Other portions were subjected to treatment with 2-ME and DTT as follows: 200 μl (20 μg HRP and 62 μg Av) were treated with 2.4 μmoles of 2-ME in 5 μl $H_2O$ (3000 fold molar excess over Av) for 1 h, followed by 24 μmoles of NEM in 100 μl of 0.1 M $NaH_2PO_4$ at pH 7.3 for 15 min. Aliquots of 52 μl (3.4 μg HRP and 10 μg Av) were subjected to HPLC. The same procedure was repeated using 2.4 μmoles of DTT.

The samples which had been set aside for control were examined after 65 h for the presence of polymer as follows: 13 μl (164 μg, 4 nmoles) of PDP-HRP and 20 μl (288 μg, 4 nmoles) of TP-Av were diluted into 400 μl of 0.1 M $NaH_2PO_4$ at pH 7.3 containing 1.4 μmoles of NEM (10 fold molar excess over thiols), and reacted for 15 min. Aliquots of 14 μl (5.6 μg HRP and 9.8 μg Av) were subjected to HPLC and the remaining solution (152 μg HRP and 268 μg Av) were chromatographed on Sepharose-4B (40 ml bed volume).

EXAMPLE 2

Copolyprotein of IgG and HSA-FL

A. Conjugation of IoG with SMCC (MCC-IoG). To 25.5 mg of lyophilized IgG dissolved in 5 ml of 50 mM $NaHCO_3$ at ph 9.0 and 0° C. was added 17 μl (0.85 μmoles) of a freshly made solution of SMCC in anhydrous dimethylformamide with rapid stirring. After 15 min the reaction mixture was neutralized with 500 μl of 1 M $NaH_2PO_4$ at pH 7.3, centrifuged at 12,000 g for 1 min, and chromatographed on G-25 (50 ml bed volume). Protein was collected in 24–30 ml of effluent, the pooled fractions concentrated to 430 μl by ultrafiltration, and the concentrate set aside on ice for characterization and utilized within 2 h. The protein concentration was 39.0 mg/ml, based upon A280 measurements and an $E_{280}^{1\%}$ of 14.0. To determine the number of protein bound 4-(N-maleimidomethyl)cyclohexane-1-carboxyl groups (MCC), the following assay was developed: 2–3 mg (12–19 nmoles) of the conjugated protein in 1 ml of PBS was reacted with 100 nmoles of 2-ME (in 10 μl H20) for 15 min, followed by reaction with 1 μmole of DTNB (in 100 μl of 1 M $NaH_2PO_4$ at pH 8.2) for 10 min. The loss of 2-ME due to reaction with protein bound maleimido groups was determined by $A_{412}$ measurements, and amounted to a stoichiometry of 3.7 moles/mole of IgG. Control experiments showed that under these conditions 2-ME did not react with unconjugated IgG. To assess whether non-covalently bound MCC had been carried through the procedure, conjugation was repeated with SMCC which had been pre-hydrolyzed in 0.1 M $NaHCO_3$ at pH 9.0 and 27° C. for 15 min, before addition of IgG. A stoichiometry of 0.5 mole of MCC/mole of IgG was obtained.

B. Thiolation of HSA-FL with SPDP (TP-HSA-FL). SPDP (1.07 ml, 41 μmoles) dissolved in anhydrous ethanol at room temperature was added during 1 min and with rapid stirring to HSA-FL (27 mg, 0.38 μmole) dissolved in 5 ml of 50 mM $NaHCO_3$ at pH 9.0 and 0° C. (solution turns cloudy). Stirring was continued for 15 min and was followed by neutralization with 500 μl of 1 M $NaH_2PO_4$ at pH 7.3. SPDP-derived disulfide bonds were next reduced with 410 μmoles of DTT in 820 μl of 0.1 M $NaH_2PO_4$ at pH 7.3 and 0° C., for 30 min. The mixture was warmed to room temperature, centrifuged, and chromatographed on G-25 (50 ml bed volume). Protein was collected in 23–30 ml of effluent, the pooled fractions were concentrated to 550 μl by ultrafiltration, and the concentrate set aside in a capped vial for characterization and utilized within 2 h. The protein concentration was 38 mg/ml based upon $A_{495}$ measurements. The TP content was determined by reacting 5 μl (190 μg) aliquots with DTNB, taking into account the $A_{412}$ contribution (about 10%) of protein bound FITC to the overall absorbance. In view of the well known propensity of albumin to bind a large number of physiological as well as non-physiological compounds (Peters, 1975), the conjugation procedure was repeated with SPDP which had been pre-hydrolyzed in 0.1 M $NaHCO_3$ at pH 9.0 and 27° C. for 15 min. A stoichiometry of 1.8 moles of TP/mole HSA-FL was obtained.

C. Copolymerization of MCC-IcG and TP-HSA-FL. Copolymerization was performed by stirring 271 μl (10.6 mg, 66 nmoles) of MCC-IgG, 308 μl (11 mg, 150 nmoles) of TP-HSA-FL, and 22 μl of 1 M $NaH_2PO_4$ at pH 7.3, for 40 h at 0°–4° C. in capped vial. For control, unreacted MCC-IgG and TP-HSA-FL were set aside as described earlier. To monitor the progress of the reaction, 17 μl (300 μg IgG and 310 μg HSA-FL) aliquots were reacted with 100 μl of PBS containing 3 μmoles of NEM (20 fold molar excess over TP) for 15 min, followed by dilution with 300 μl of PBS containing 0.2%(w/v) SDS, centrifugation, and chromatography on Sepharose-4B (50 ml bed volume) in PBS containing 0.1%(w/v) SDS. After 40 h of reaction the copolymerization mixture was divided in 2 portions: portion one (185 μl, 6.2 mg) was chromatographed on Sepharose-4B (50 ml bed volume), and a polymeric peak was collected in 16–19 ml of effluent. Its protein content and composition were determined by $A_{495}$ and $A_{280}$ measurements, and its TP content by reaction with DTNB. Portion two (220 μl, 7.5 mg) was reacted with 800 μl of PBS containing 33 μmoles of NEM (20 fold molar excess over TP) for 30 min at 0° C., and chromatographed on Sepharose-4B (50 ml bed volume). A polymeric peak was collected in 16–19 ml of effluent, and its protein content and composition determined. Aliquots were treated with 2-ME and DTT as follows: 200 μl (144 μg of IgG and 60 μg of HSA-FL) was treated with 2.5 μmoles of 2-ME (3000 fold molar excess over HSA-FL) for 1 h, followed by 25 μmoles of NEM in 87 μl of 0.1 M $NaH_2PO_4$ at pH 7.3 for 15 min. Aliquots of 35 μl (9.4 μg of HSA-FL and 22 μg of IgG) were subjected to HPLC. The same procedure was repeated using 2.5 μmoles of DTT in place of 2-ME.

The samples which had been set aside for control were examined after 40 h for the presence of polymers as follows: 19 μl of TP-HSA-FL (754 μg, 10 nmoles) was reacted with 7 μmoles of NEM (20 fold molar excess over thiols) in 100 μl of PBS for 30 min, followed by addition of 19 μl of MCC-IgG (741 μg, 4.6 nmoles). Aliquots of 57 μl (310 μg of HSA FL and 306 μg of IgG) were chromatographed on Sepharose-4B (50 ml bed volume) in PBS containing 0.1%(w/v) SDS.

EXAMPLE 3

Copolymerization of MCC-HSA and TP-HSA-FL

A. Conjugation of HSA with SMCC (MCC-HSA). To 22 mg of lyophilized HSA dissolved in 4 ml of 50 mM $NaHCO_3$ at pH 9.0 and 0° C. was added 66 μl (2.64 μmoles) of a freshly prepared solution of SMCC in anhydrous dimethylformamide with rapid stirring.

After 15 min. the reaction mixture was neutralized with 400 μl of 1 M NaH$_2$PO$_4$ at pH 7.3, centrifuged at 12,000 g for 1 min, and chromatographed on a column (50 ml bed volume) of Sephadex G-25. Protein was collected in 24-30 ml of effluent and the pooled fractions concentrated to 400 μl by ultrafiltration. The protein concentration was 45 mg/ml, based upon A$_{280}$ measurements and an E$_{280}$$^{1\%}$ of 5.31. The number of protein-bound MCC groups, which was determined as described earlier, was 3.2 MCC groups per molecule of HSA.

B. Preparation of TP-HSA-FL. TP-HSA-FL was prepared as in Example 2B.

C. Copolymerization of MCC-HSA and TP-HSA-FL. Copolymerization was performed by stirring 300 μl (13.5 mg, 202 nmoles) of MCC-HSA, 205 μl (14.3 mg, 202 nmoles) of TP-HSA-FL, and 50 μl of 1 M NaH$_2$PO$_4$ at pH 7.3, for 21 h at 0°-4° C. in a capped vial. The progress of the reaction was monitored as described earlier, by chromatography on a column of Sepharose-4B in PBS containing 0.1% (w/v) SDS. At the end of 21 hours of reaction, the copolymerization reaction mixture was chromatographed on a column of Sepharose-4B in PBS. A polymeric peak was collected in 17-22 ml of effluent; its protein content and composition were determined by A$_{495}$ and A$_{280}$ measurement and its TP content by reaction with DTNB as described above. There were 1.3 TP-HSA-FL units per MCC-HSA unit in the polyprotein.

I claim:

SCHEMES

In the following schemes:

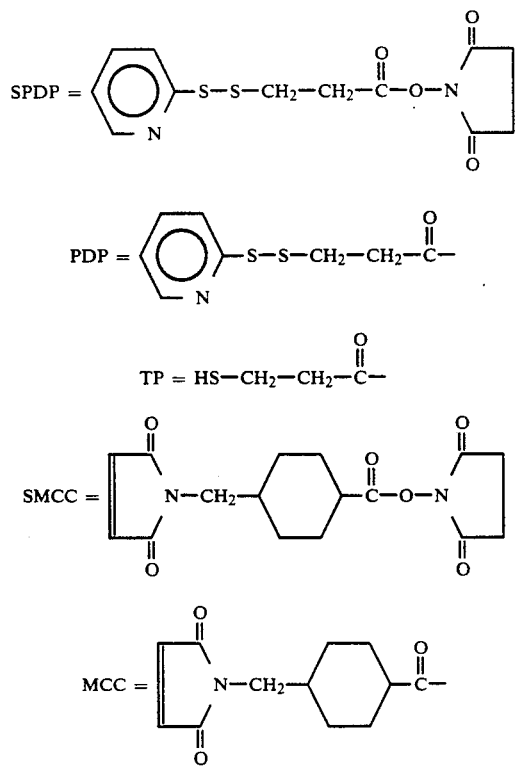

SCHEME 1

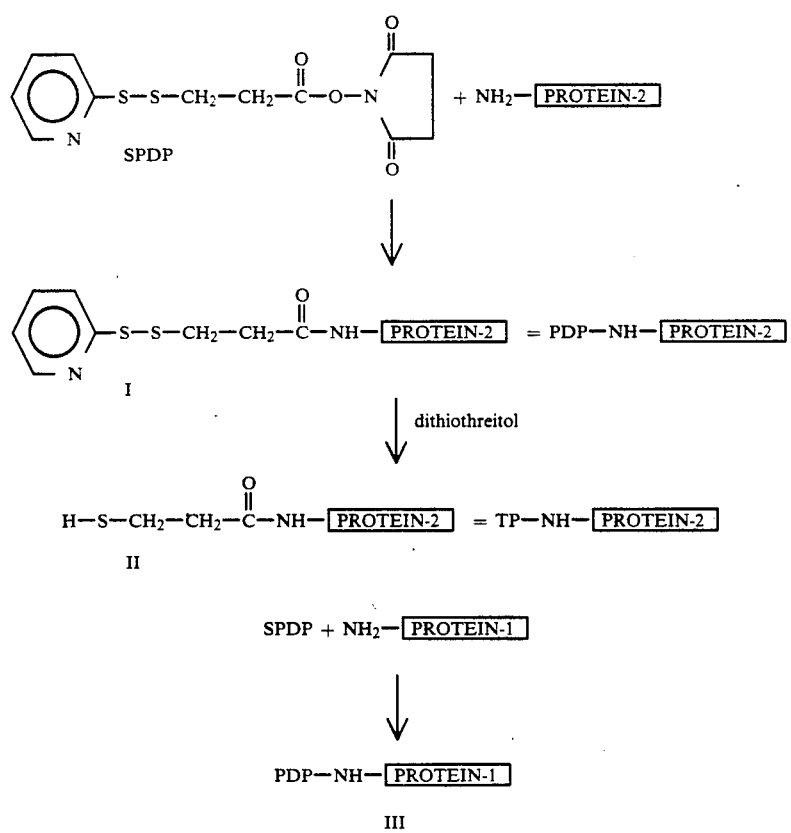

SCHEME 1

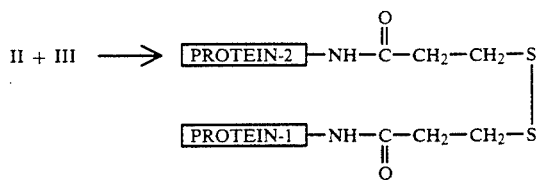

SCHEME 2

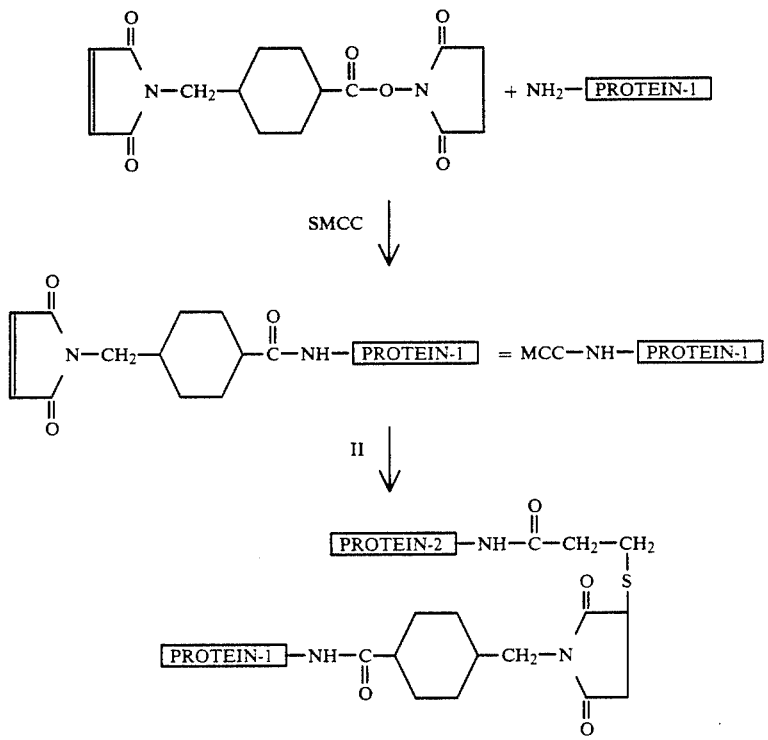

1. A method for producing a polyprotein having at least 10 units held together by sulfur to sulfur or sulfur to carbon bonds, each unit comprising a protein and one or more heterobifunctional reagents capable of forming a covalent bond with an amino group wherein at least one of the heterobifunctional reagents is capable of forming a covalent sulfur-sulfur or carbon-sulfur bond with a thiol group and at least one of the reagents has a thiol group or a group capable of being converted into a thiol group, the method comprising the steps of:
   a) forming a first protein-heterobifunctional reagent complex by treating a first protein with a sufficient amount of a heterobifunctional reagent so as to form a covalent bond between amino groups of the first protein and 3 to 5 molecules of the reagent per protein molecule;
   b) forming a second protein-heterobifunctional reagent complex by treating a second protein with a sufficient amount of a heterobifunctional reagent so as to form a covalent bond between amino groups of the second protein and at least 5 molecules of the reagent per protein unit;
   c) providing a thiol group on at least one of the reagents; and
   d) joining the first protein-heterobifunctional reagent complex and the second protein-heterobifunctional reagent complex by forming sulphur-sulphur or carbon-sulphur bonds into a polyprotein having at least 10 units.

2. The method of claim 1 wherein the polyprotein is soluble in water.

3. The method of claim 1 wherein the second protein is treated with a sufficient amount of a heterobifunctional reagent so as to form a covalent bond between the amino groups of the second protein and at least 20 molecules of the reagent per protein unit.

4. The method of claim 1 wherein the second protein is treated with a sufficient amount of a heterobifunctional reagent so as to form a covalent bond between the amino groups of the second protein and at least 35 molecules of the reagent per protein unit.

5. The method of claim 1 wherein the second protein is treated with a sufficient amount of a heterobifunctional reagent so as to form a covalent bond between the amino groups of the second protein and 20–35 molecules of the reagent per protein unit.

6. The method of claim 1 wherein the polyprotein has 10 to 100 protein units.

7. The method of claim 1 wherein the first protein and the second protein are the same.

8. The method of claim 1 wherein the first protein and the second protein are different.

9. The method of claim 8 wherein the ratio of the first protein to the second protein is 1:0.25 to 1:10.

10. The method of claim 8 wherein the ratio of the first protein to the second protein is 1:1 to 1:4.

11. The method of claim 1 wherein the polyprotein elutes in the exclusion volume of a Sepharose 4B chromatographic column.

12. The method of claim 1 wherein the polyprotein has a molecular weight of at least $2 \times 10^6$.

13. The method of claim 1 wherein the polyprotein has a molecular weight of at least $10 \times 10^6$.

14. The method of claim 1 wherein the molecular weight of the protein is at least $20 \times 10^6$.

15. The method of claim 8 wherein the first protein is albumin, and the second protein is immunoglobulin.

16. The method of claim 1 wherein the polyprotein contains an average of at least 1 reactive group per protein unit.

17. The method of claim 16 further comprising the step of treating reactive groups on the polyprotein with molecules having thiol groups, or thiol groups on the polyprotein with molecules having reactive groups.

18. The method of claim 17 wherein the molecules having thiol or reactive groups are oligopeptides, polypeptides or proteins.

19. The method of claim 17 wherein the molecules are monoclonal antibodies.

20. The method of claim 17 wherein the molecules are monoclonal antibodies and cytotoxins.

21. The method of claim 17 wherein the molecule is a hormone.

22. The method of claim 17 wherein the molecules are detection proteins.

23. The method of claim 17 wherein the molecules bind to avidin.

24. The method of claim 23 wherein the molecule is biotin

25. The method of claim 8 wherein one of the first protein or the second protein binds to biotin and the other of the first protein or the second protein is a detection proteins.

26. The method of claim 25 wherein the first protein that binds to biotin is avidin.

27. The method of claim 25 wherein the detection protein is selected from the group consisting of horseradish peroxidase, alkaline phosphatase, galactosidase, glucose oxidase, and luciferase.

28. The method of claim 26 wherein the detection agent is horseradish peroxidase.

29. A polyprotein prepared by the method of claim 1.

30. A polyprotein that has substantially the solubility properties of its component protein units, and that contains at least 10 protein units having molecular weight greater than $1 \times 10^4$, said polyprotein is formed by a method comprising forming a first protein-heterobifunctional reagent complex, forming a second protein-heterobifunctional reagent complex, and joining said first protein-heterobifunctional reagent complex and said second protein-heterobifunctional reagent complex.

31. The polyprotein of claim 30 wherein the protein units consist essentially of a single protein.

32. The polyprotein of claim 30 wherein said polyprotein has molecular weight equal to or less than $100 \times 10^6$.

33. The polyprotein of claim 30 wherein the protein units consist essentially of two different proteins.

34. The polyprotein of claim 33 wherein the ratio of the different proteins is 1:0.25 to 1:10.

35. The polyprotein of claim 30 wherein the polyprotein contains between 10 and 100 protein units.

36. The polyprotein of claim 30 wherein the molecular weight of the polyprotein is at least two million.

37. The polyprotein of claim 30 wherein the polyprotein contains an average of at least one reactive group per protein unit.

38. The polyprotein of claim 37 wherein the process of producing the polyprotein further comprising the step of treating reactive groups on the polyprotein with molecules having thiol groups, or thiol groups on the polyprotein with molecules having reactive groups wherein plurality of reactive groups or thiol groups derived from reactive groups are covalently bonded with molecules having thiol groups or reactive groups, 39. The polyprotein of claim 38 wherein the molecules are oligopeptides, polypeptides, or proteins.

40. The polyprotein of claim 39 wherein the molecules are monoclonal antibodies.

41. The polyprotein of claim 39 wherein the molecules are hormones.

42. The polyprotein of claim 39 wherein the molecules are detection proteins.

43. The polyprotein of claim 39 wherein the molecules are monoclonal antibodies and cytotoxins.

44. The polyprotein of claim 39 wherein the molecules bind to biotin.

45. The polyprotein of claim 30 wherein at least one of the protein units is albumin.

46. A method for producing a polyprotein having at least 10 units as described in claim 1, wherein said heterobifunctional reagent is selected from the group consisting of SPDP and SMCC.

47. A method for producing a polyprotein having at least 10 units, as recited in claim 1, wherein said heterobifunctional reagent is SPDP.

48. A method for producing a polyprotein having at least 10 units, as recited in claim 1, wherein said heterobifunctional reagent is SMCC.

* * * * *